United States Patent
Glazer

(10) Patent No.: US 8,656,924 B2
(45) Date of Patent: *Feb. 25, 2014

(54) METHODS AND DEVICES FOR RETAINING SURGICAL INSTRUMENTS AND CABLES WITHIN STERILE FIELDS

(75) Inventor: Paul A. Glazer, Chestnut Hill, MA (US)

(73) Assignee: Tenzin, LLC, Chestnut Hill, MA (US)

( * ) Notice: Subject to any disclaimer, the term of this patent is extended or adjusted under 35 U.S.C. 154(b) by 637 days.

This patent is subject to a terminal disclaimer.

(21) Appl. No.: 12/912,408

(22) Filed: Oct. 26, 2010

(65) Prior Publication Data

US 2011/0034923 A1    Feb. 10, 2011

Related U.S. Application Data

(63) Continuation of application No. 12/398,667, filed on Mar. 5, 2009.

(60) Provisional application No. 61/033,804, filed on Mar. 5, 2008.

(51) Int. Cl.
*A61B 19/08* (2006.01)
*A61F 5/37* (2006.01)
*A61B 18/18* (2006.01)

(52) U.S. Cl.
USPC ............. 128/852; 128/849; 128/846; 606/41

(58) Field of Classification Search
USPC ......... 606/1, 32, 33, 49, 139, 144, 41, 42, 48; 227/175.1; 128/849, 852, 898, DIG. 15; 248/690–692

See application file for complete search history.

(56) References Cited

U.S. PATENT DOCUMENTS

| | | | |
|---|---|---|---|
| 3,804,093 A * | 4/1974 | Fell | 604/355 |
| 4,174,816 A | 11/1979 | Olson | |
| 5,010,899 A * | 4/1991 | Thompson | 128/849 |
| 5,074,863 A | 12/1991 | Dines | |
| 5,178,619 A | 1/1993 | Galazaka | |
| 5,916,215 A * | 6/1999 | Long et al. | 606/41 |
| 6,379,178 B1 | 4/2002 | Jones, III et al. | |
| 6,905,496 B1 * | 6/2005 | Ellman et al. | 606/41 |
| 7,168,538 B2 | 1/2007 | Pena | |
| 7,862,562 B2 * | 1/2011 | Eberl | 606/41 |

OTHER PUBLICATIONS

Web page: www.whitneyblake.com/AWC/cabass.html; Adirodack Wire & Cable—Custom Cable Assemblies; Nov. 20, 2007.

(Continued)

*Primary Examiner* — Emily Schmidt
*Assistant Examiner* — Bradley G Thomas, Jr.
(74) *Attorney, Agent, or Firm* — Edwards Wildman Palmer LLP; Joshua L. Jones

(57) ABSTRACT

The subject devices and methods retain surgical instruments and sterile portions of any accompanying cables within sterile surgical fields. One such surgical device includes a surgical instrument for performing surgical procedures within a sterile field. A cable is attached to the surgical instrument for connecting the surgical instrument located within the sterile field to support equipment located outside the sterile field. A self-retracting coil is operatively connected to the surgical instrument. The self-retracting coil is adapted and configured to be anchored within the sterile field to ensure that the surgical instrument and the sterile portion of the cable remain within the sterile field during performance of the surgical procedure.

6 Claims, 7 Drawing Sheets

(56) References Cited

OTHER PUBLICATIONS

Web page: www.pemed.com/dental/dental/htm; Product Engineering—Medical Equipment Division; Dental duplicators; Nov. 20, 2007.

Web page: www.meyerwire.com/Applications.html; Meyer Wire & Cable Company, LLC; Designer and Manufacturers of Custom Cable and Coil Cords; Nov. 20, 2007.

Web page: www.autacusa.com/catalog.asp; Autac Re-Trak-Tul Kords; Retractable Power Cords and Coil Cords; Nov. 20, 2007.

Web page: www.neisystems.com/molded-cable-assemblies/index.shtml; New England Interconnect Systems, Inc.; Molded Cable Assemblies; Nov. 20, 2007.

Promotional material; C&M Corporation, Waureganm CT 06387; Cable and assemblies for medical applications; Form #BR MED 0105.

Web page: www.neisystems.com/orthopedic-drill-and-medical-foot-pedal.html; New England Interconnect Systems, Inc.; Orthopedic Drill Cable; Nov. 20, 2007.

* cited by examiner

METHODS AND DEVICES FOR RETAINING SURGICAL INSTRUMENTS AND CABLES WITHIN STERILE FIELDS

CROSS-REFERENCE TO RELATED APPLICATIONS

This application is a continuation of U.S. patent application Ser. No. 12/398,667 filed Mar. 5, 2009 which claims benefit of priority to U.S. Provisional Patent Application No. 61/033,804, filed Mar. 5, 2008, which are incorporated by reference herein in their entirety.

BACKGROUND OF THE INVENTION

1. Field of the Invention

The present invention relates to surgical instruments, and more particularly, to surgical instruments having cords or cables connecting the instrument within a sterile field to equipment outside the sterile field.

2. Description of Related Art

A variety of surgical devices are known in the art for performing modern surgery. Of such devices, many are directed to surgical instruments connected to support equipment by cords including electrical cords, optical fibers, tubes, hoses, or other types of cables. Typically, the surgical instrument is used within the sterile field of a surgery with the support equipment outside the sterile surgical field. Great care must be taken to assure the instrument and portions of its cable that are within the sterile field remain sterile. It is also important to prevent non-sterile portions of the cable from entering the sterile field. However, it is not uncommon for sterile portions of the cable to hang down out of the sterile field raising the question of whether they are contaminated as the instrument is moved during surgery. It is also not uncommon for the instrument to fall out of the sterile field, often dragged by the weight of its own cable.

For example, one such instrument commonly used in surgery is the electrocautery pencil, which is used to cut and coagulate tissue during surgery. Typically electrocautery pencils are kept sterile by clipping a plastic holster to the sterile drape. When not in use, the device is placed into the holster until needed again. However, there are frequently problems with a surgeon missing the holster or otherwise dropping the instrument and/or its cord out of the sterile field. When this happens, a new, sterile electrocautery pencil and cord must be obtained for use during the remainder of the procedure.

The efforts required for keeping instruments and their respective cables within the sterile field add to the stress and fatigue experienced by surgeons and nurses/assistants during surgery, and can therefore lead to fatigue and stress induced complications during surgery. Moreover, when an instrument is lost from the sterile field and must be replaced, attention is taken away from the surgical task at hand and the resulting distraction can lead to complications. The delay caused by having to replace an instrument at a critical time during a procedure can further lead to complications.

Some solutions have been proposed for dealing with the issue of instrument cables in the sterile field during surgery. U.S. Pat. No. 4,174,816 to Olson describes a retractor device for cords of surgical instruments, which has a housing with several spring loaded reel pulleys for allowing the cord to be withdrawn and retracted as needed. U.S. Pat. No. 5,178,619 to Galazaka describes another device for reeling surgical cords in and out that uses a ratchet mechanism to control when the reel retracts the cord. While these devices can be used to help keep instruments and cords within sterile fields, they add considerable bulk to the surgical instruments, and if designed to be reusable, they add to the cost of sterilization. One solution to the cost problem is provided in U.S. Pat. No. 5,074,863 to Dines, which describes a disposable surgical cord reel. However, the device described by Dines still adds considerable bulk to the surgical instrument being used.

Such conventional methods and systems of keeping surgical devices and sterile portions of their cables within a sterile field have been generally considered satisfactory for their intended purpose. However, it would be beneficial to provide a way of reliably keeping sterile portions of surgical instruments within a sterile field. It would also be beneficial to provide systems and methods that can keep sterile portions of surgical devices within a sterile field with minimal effort on the part of surgeons and nurses/assistants during surgery, without adding considerable bulk and cost. The present invention provides a solution for these problems.

SUMMARY OF THE INVENTION

The subject invention includes a new and useful surgical device having a surgical instrument for use in performing a surgical procedure within a sterile field. A cable is attached to the surgical instrument for connecting the surgical instrument located within the sterile field to support equipment located outside the sterile field. A self-retracting coil is operatively connected to the surgical instrument. The self-retracting coil is adapted and configured to be anchored within the sterile field to ensure that the surgical instrument and a sterile portion of the cable remain within the sterile field during performance of the surgical procedure.

The self-retracting coil can form a section of the cable of the surgical instrument, or can be provided as a separate attachment. Anchoring means can be attached to the cable proximate the self-retracting coil thereof, wherein the anchoring means are configured and adapted to anchor the cable within the sterile field. The surgical instrument can be an electrocautery pencil, cauterizing forceps, surgical drill, suction device, mono-polar or bi-polar RF cutting and/or coagulating instruments (such as LigaSure™ instruments available from Valleylab, a division of Tyco Healthcare Group LP, of Boulder, Colo.), ultrasonic cutting and/or coagulating instruments (such as Harmonic Scalpel® available from Ethicon Endo-Surgery, Inc. of Cincinnati, Ohio), or any other suitable surgical instrument.

A surgical anchoring system is also provided, including a self-retracting coil and first anchoring means attached to a proximal end of the coil. The first anchoring means are configured and adapted to anchor the coil within a sterile field. Second anchoring means are attached to a distal end of the coil. The second anchoring means are configured and adapted to attach the coil to a surgical device to ensure that a surgical instrument and sterile portions of a cable of the surgical device remain within the sterile field during performance of a surgical procedure.

Another exemplary surgical device includes a surgical instrument for use in performing a surgical procedure within a sterile field. A hook and latch fastener having a hook portion and a latch portion is provided, wherein one of the hook and latch portions is attached to the surgical instrument. The other of the hook and latch portions is configured and adapted to be attached to a structure within the sterile field for parking the surgical instrument between uses during a surgical procedure.

A method is provided for keeping a surgical instrument and attached cable within a sterile surgical field. The method includes providing a surgical instrument attached to a cable configured to connect the surgical instrument located within a sterile field to support equipment located outside the sterile field. The method also includes anchoring the cable to a substantially fixed structure within the sterile field and providing retention means for use within the sterile field in keeping the surgical instrument and sterile portions of the cable within the sterile field in the event of the instrument being dropped during performance of a surgical procedure.

These and other features and benefits of the devices and methods of the subject invention and the manner of retaining surgical instruments and sterile portions of accompanying cables within a sterile field will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the devices and methods of retaining surgical instruments and accompanying cables within a sterile field according to the subject invention without undue experimentation, preferred embodiments thereof will be described in detail hereinbelow with reference to certain figures, wherein.

DETAILED DESCRIPTION OF THE PREFERRED EMBODIMENT

Figure 1:
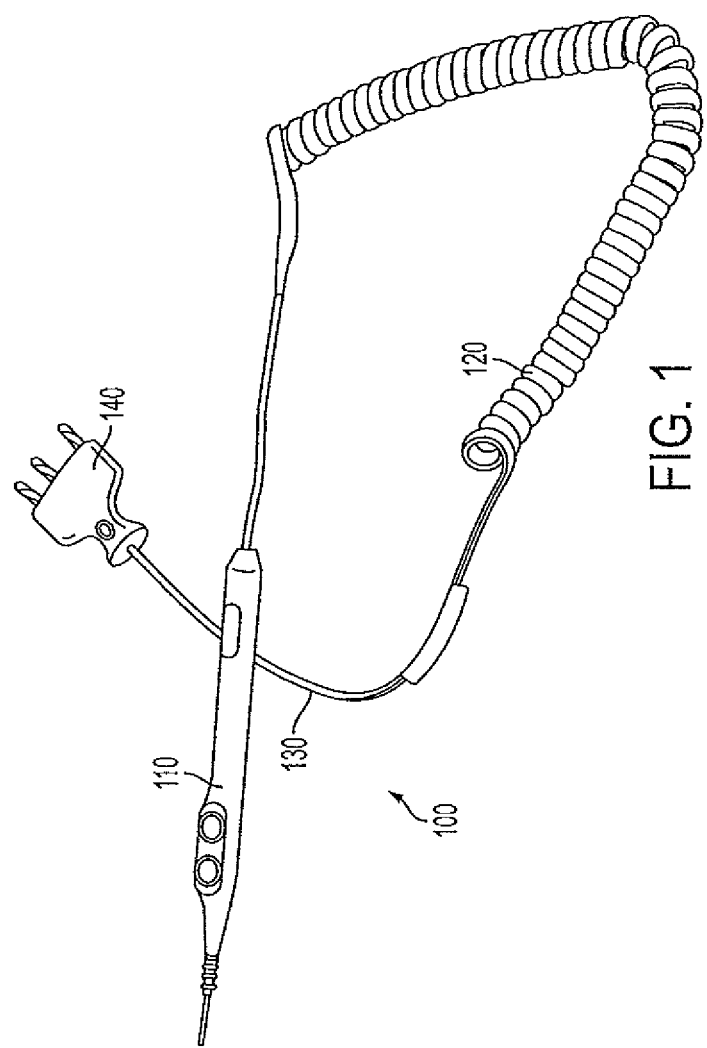
FIG. 1 is a perspective view of a representative embodiment of a surgical instrument in accordance with the present invention, showing a self-retractable coil section in the cord for use in retaining the surgical instrument within a sterile field.

Referring now to the drawings, wherein like reference numerals identify or otherwise refer to similar structural features or elements of the various embodiments of the subject invention, there is illustrated in FIG. 1 a surgical device for retaining a surgical instrument and accompanying cable within a sterile field, designated generally by reference character 100. Other embodiments of a surgical device in accordance with the invention, or aspects thereof, are depicted in FIGS. 2-7, as will be described below.

Figure 2:
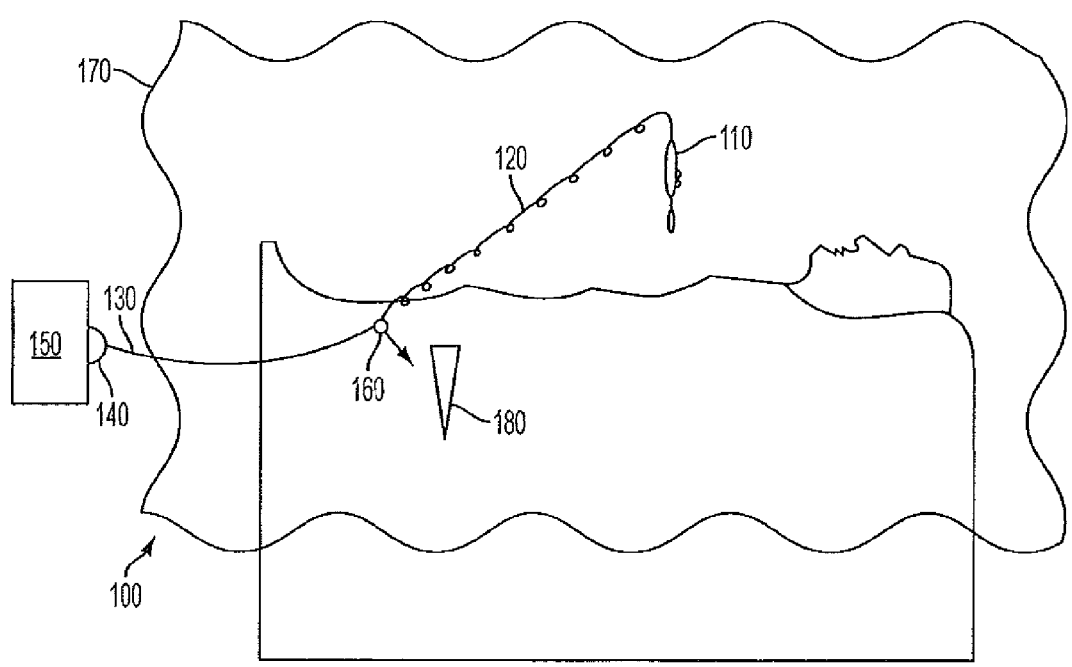
FIG. 2 is a schematic view of the instrument of FIG. 1 in accordance with the present invention, showing the instrument in use with the coil extended within a sterile field during surgery.

With reference now to FIG. 1, surgical device 100 includes a typical electrocautery pencil 110 having an electrical cord 130 and connector 140 for connecting electrocautery pencil 110 to power source 150 (shown in FIG. 2). A section of cord 130 proximate electrocautery pencil 110 includes a self-retracting coil 120.

Referring now to FIG. 2, surgical device 100 is shown schematically with electrocautery pencil 110 and coil 120 extended within a sterile field 170, as when in use during surgery. Cord 130 is anchored with a fastener or clip 160 to a relatively fixed anchor point, such as a secure drape or surgical blanket over the patient, or other suitable structure within sterile field 170. Connector 140 at the proximal end of cord 130 connects electrocautery pencil 110 to power source 150.

Figure 3:
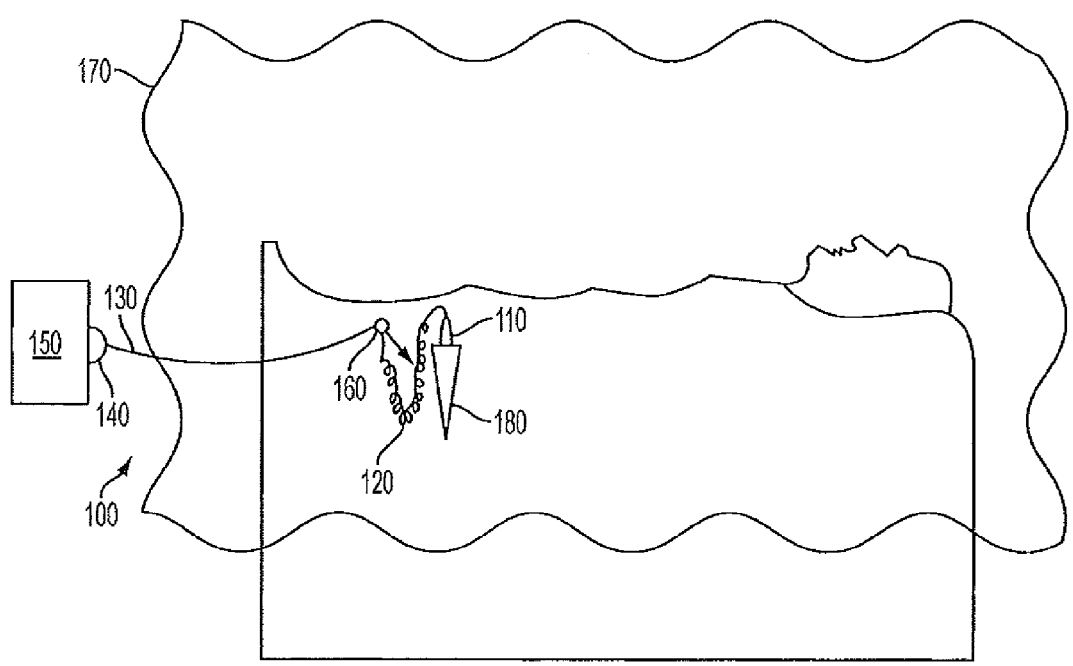
FIG. 3 is a schematic view of the instrument of FIG. 1 in accordance with the present invention, showing the instrument parked in a holster, with the self-retracting cable retracted.

During surgery, power source 150, connector 140, and a portion of cord 130 proximate power source 150 remain outside sterile field 170, while electrocautery pencil 110 and coil 120 remain inside sterile field 170. Between uses during a surgical procedure, electrocautery pencil 110 can be parked in holster 180, which is attached to a suitable surface, e.g. a drape, within sterile field 170, as shown in FIG. 3. The portion of cord 130 between clip 160 and power source 150 remains virtually unmoved regardless of whether electrocautery pencil 110 is parked or is in use. When parked, coil 120 retracts itself to take up slack so that none of cord 120/130 drops below the bottom of sterile field 170. Thus the non-sterile portion of cord 130 remains outside sterile field 170, and the sterile portion of cord 130 remains inside sterile field 170 at all times during surgery.

It is also possible to fix anchor 160 high enough within sterile field 170 so that if electrocautery pencil 110 is accidentally dropped coil 120 retracts itself sufficiently to prevent electrocautery pencil 110 from falling out of sterile field 170. For that matter, holster 180 is optional, since coil 120 and anchor 160 can be configured to park electrocautery pencil by freely hanging from anchor 160 within sterile field 170 when not in use, by fixing anchor 160 high within sterile field 170, for example.

Figure 4:
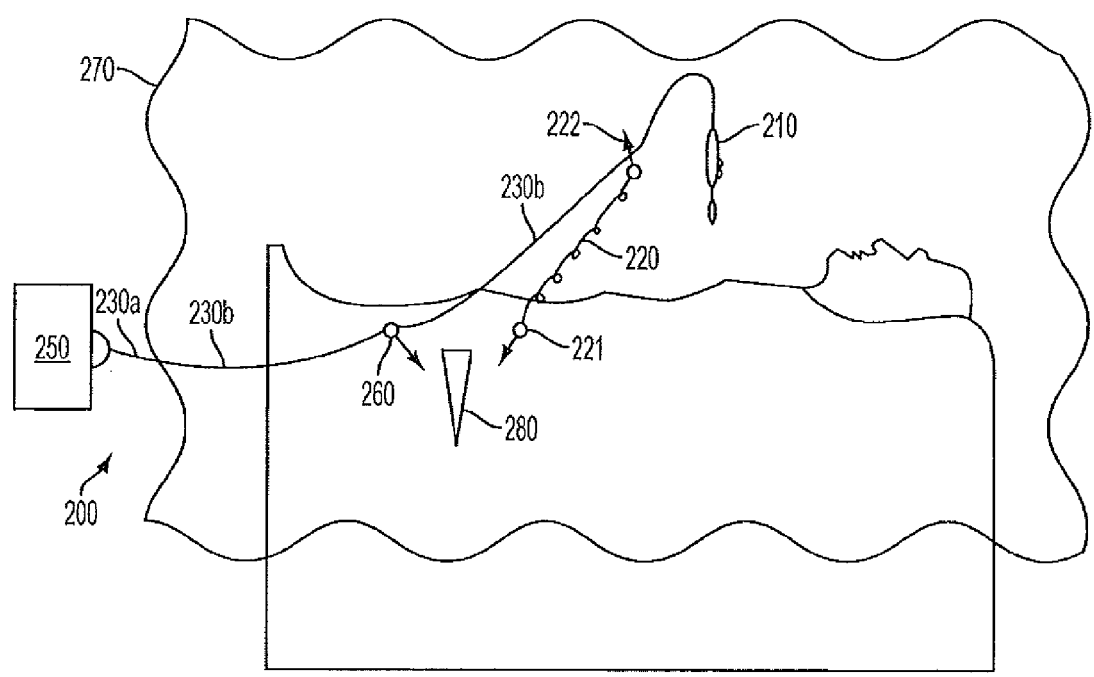
FIG. 4 is a schematic view of an exemplary embodiment of a surgical anchoring system in accordance with the present invention, showing the self-retracting coil anchored within the surgical field and attached to the surgical instrument, with the coil extended when the instrument is in use during surgery.

FIG. 4 shows an exemplary embodiment of a surgical anchoring system 200 for use with a standard electrocautery pencil 210. Electrocautery pencil 210 is connected to power source 250 by cable 230a,b. Anchor 260 anchors cable 230a,b to a suitable surface within sterile field 270, with a non-sterile cord section 230a outside sterile field 270 and a sterile cord section 230b inside. A self-retracting coil 220 has an anchor 221 at one end for attaching to a suitable surface within sterile field 270. A connector 222 at the opposite end of coil 220 attaches coil 220 to electrocautery pencil 210, or preferably to sterile cord section 230b. Alligator clips, pins, or other suitable fasteners can be used as anchors or connectors 221/222. As shown in FIG. 4, when electrocautery pencil 210 is in use, coil 220 can freely stretch as needed.

Figure 5:
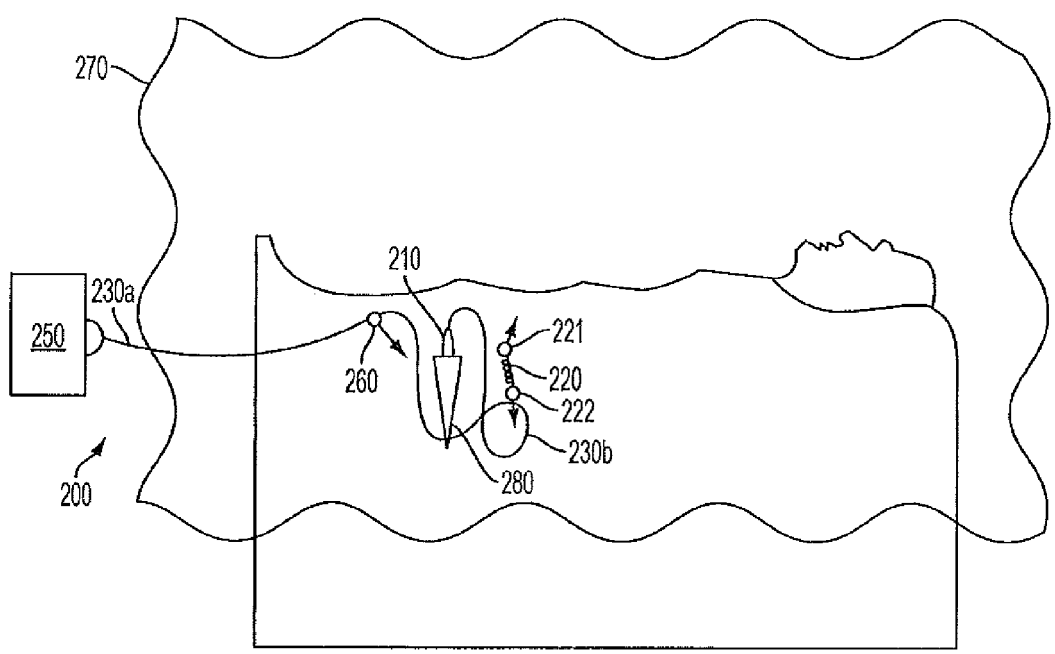
FIG. 5 is a schematic view of the surgical anchoring system of FIG. 4 in accordance with the present invention, showing the self-retracting coil retracted within the sterile field to retain the sterile portion of the cord within the sterile field while the instrument is parked within a holster during surgery.

FIG. 5 shows electrocautery pencil 210 parked within holster 280 within sterile field 270 between uses during a surgical procedure. Coil 220 retracts, bringing sterile cord section 230b towards anchor 221 thus retaining cord 230b within sterile field 270. In this way, the weight of cord 230a,b cannot pull electrocautery pencil 210 out from holster 280 when parked. As with device 100 described above, holster 280 is optional, since in many situations coil 220 can be anchored high enough and can be attached to cord 230b in such a way as to allow electrocautery pencil 210 to park by hanging freely from anchor 221 without leaving sterile field 270. Coil 220 can be used to retain a standard electrocautery pencil and sterile cord section within the sterile field at all times, even when dropped, and does not require redesign or special manufacture or retooling for existing electrocautery pencil designs.

A wide variety of different suitable self-retracting coil configurations can be used for coils 120, 220. The coil diameter, stiffness, and length can be varied as appropriate for particular instruments, procedures, or operating environments. Those skilled in the art will readily appreciate that any suitable self-retracting coil configuration can be used without departing from the spirit and scope of the invention.

Figure 6:
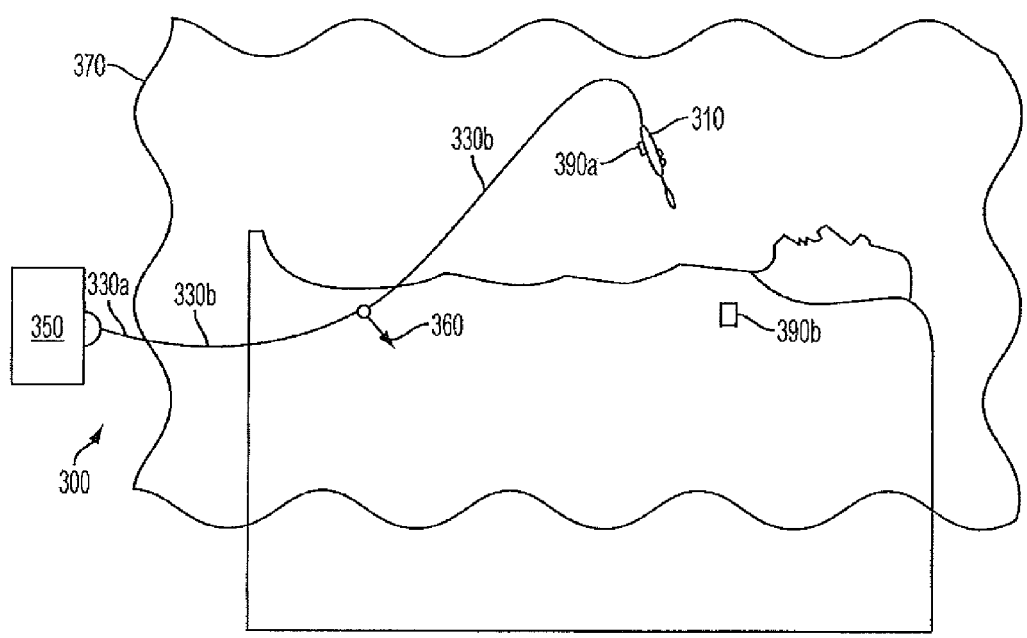
FIG. 6 is a schematic view of another exemplary embodiment of an instrument in accordance with the present invention, showing one portion of a hook and latch anchor adhered to the instrument, and the other portion attached to an anchor point within the sterile field.

With reference now to FIG. 6, another exemplary surgical device 300 is shown having electrocautery pencil 310 connected to power source 350 through cord 330*a,b*. Anchor 360 attaches cord 330*a,b* to a suitable surface of sterile field 370 to keep sterile section 330*b* within sterile field 370, and to keep non-sterile section 330*a* outside. Hook and latch anchor 390*a,b* is provided for parking electrocautery pencil 310 when not in use. One half 390*a* of hook and latch anchor 390*a,b* is adhered or otherwise attached to a suitable surface of electrocautery pencil 310. The other half 390*b* is adhered, sewn, or otherwise attached to an appropriate surface within sterile field 370.

Figure 7:
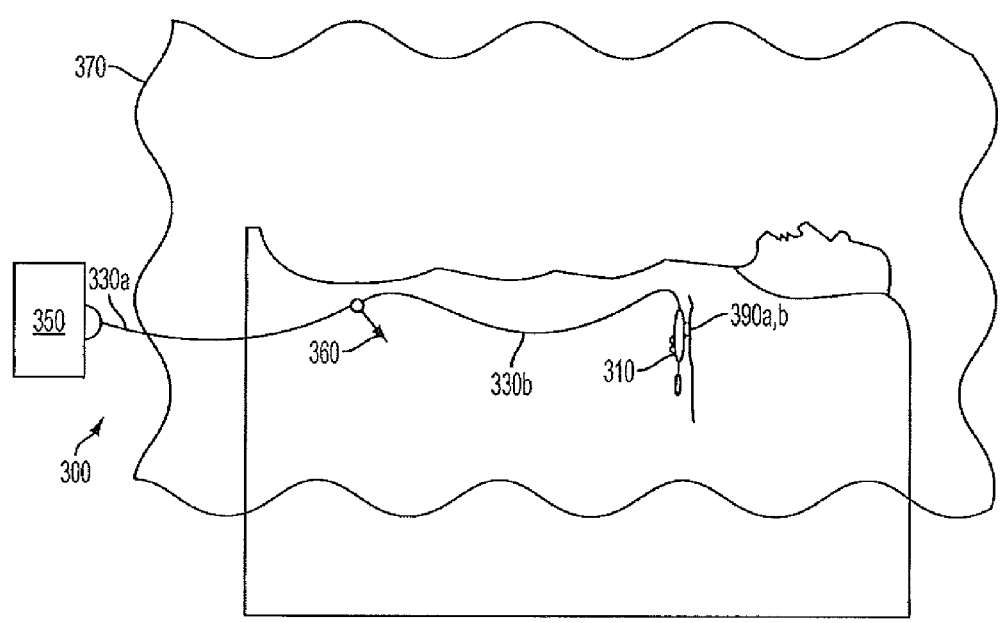
FIG. 7 is a schematic view of the instrument of FIG. 6 in accordance with the invention, showing the instrument parked by attachment of the two portions of the hook and latch anchor.

Between uses of electrocautery pencil 310 during surgery, electrocautery pencil 310 can be parked by attaching the two halves of hook and latch anchor 390*a,b*, as shown in FIG. 7. Exemplary hook and latch fasteners for this application include Velcro® fasteners available from Velcro USA Inc., of Manchester, N.H. Hook and latch anchor 390*a,b* can be located so as to retain sterile cord section 330*b* within sterile field 370 when electrocautery pencil 310 is parked. It is also contemplated that hook and latch anchor 390*a,b* can be used in conjunction with self-retracting coils (e.g. coils 120, 220 described above) to retain an electrocautery pencil within a sterile field when dropped.

It is envisioned that hook and latch anchor 390*a,b* can be sized and shaped to be provided as a sterilized accessory unit, including adhesive portions with removable covers. One of the removable covers can be removed to adhere anchor 390*a,b* to an electrocautery pencil, and the other can be removed to adhere to an appropriate surface within sterile field 370. It is also contemplated that anchor 390*a,b* can be provided pre-attached to either an electrocautery pencil or to a surface (e.g. a drape) within the sterile field, with an adhesive layer of the non-preattached portion of anchor 390*a,b* covered with a removable cover to be removed for attachment to the remaining one of the electrocautery pencil or surface within the sterile field. It is also possible for one half of anchor 390*a,b* to be sewn to a drape used within a sterile field, with the other half of anchor 390*a,b* being provided pre-attached to a surgical instrument, e.g. electrocautery pencil 310. It is not necessary for both halves of hook and latch anchor 390*a,b* to be the same size or shape. For example, it can be advantageous for portion 390*a* to wrap substantially all the way around electrocautery pencil 310, and/or for portion 390*b* to be significantly larger than portion 390*a* to make it easier for a surgeon to park electrocautery pencil 310 without missing. Moreover, portion 390*a* can be attached directly on electrocautery pencil 310, or on cord 330*a,b*.

While these configurations are exemplary, those skilled in the art will readily appreciate that any suitable arrangement of hook and latch anchor or equivalent fastener can be used without departing from the spirit and scope of the invention. Furthermore, hook and latch anchor 390*a,b* can be used advantageously with or without a holster (e.g. holster 180, 280), and with or without a self-retractable coil (e.g. coil 120, 220). Those skilled in the art will readily appreciate that anchor 390*a,b* can also be used for non-corded instruments such as suturing instruments, clip appliers, staplers, or any other suitable cordless instrument.

The systems and methods of retaining surgical instruments and cables within sterile fields have been described above in the context of electrocautery pencils and accompanying power cords. However, those skilled in the art will readily appreciate that in addition to electrocautery pencils, cauterizing forceps, surgical drills, suction devices, mono-polar or bi-polar RF cutting and/or coagulating instruments (such as LigaSure™ instruments available from Valleylab, a division of Tyco Healthcare Group LP, of Boulder, Colo.), ultrasonic cutting and/or coagulating instruments (such as Harmonic Scalpel® available from Ethicon Endo-Surgery, Inc. of Cincinnati, Ohio), or any other suitable instrument can be used without departing from the spirit and scope of the invention. Moreover, electrical cords, fiber optic cables, hoses, suction tubes, drains mechanical linkage cables, or any other suitable type of cable or elongate flexible element can be retained within a sterile field using the systems and methods as described above. Similarly, those skilled in the art will readily appreciate that any suitable support structure or equipment, including wall fixtures and outlets, can be used as appropriate in lieu of power source 150, 250, 350, depending on what type of surgical instrument is used.

While the apparatus and methods of the subject invention have been shown and described with reference to preferred embodiments, those skilled in the art will readily appreciate that various changes and/or modifications may be made thereto without departing from the spirit and scope of the subject invention as defined by the appended claims.

What is claimed is:

1. A surgical device comprising: a) a surgical instrument for use in performing a surgical procedure within a sterile field; and b) a hook and latch fastener having a hook portion and a latch portion, wherein one of the hook and latch portions is attached to the surgical instrument, wherein the other of the hook and latch portions is configured and adapted to be attached to a structure within the sterile field for parking the surgical instrument between uses during a surgical procedure; and wherein the hook and latch portion attached to the surgical instrument wraps substantially around a portion of the surgical instrument.

2. A surgical device as recited in claim 1, wherein the hook and latch portion that is configured and adapted to be attached to a structure within the sterile field for parking the surgical instrument is larger than the hook and latch portion attached to the surgical instrument.

3. A surgical device as recited in claim 1, wherein the hook and latch portion attached to the surgical instrument is attached to a cord portion of the surgical instrument.

4. A surgical device as recited in claim 1, wherein the hook and latch portion attached to the surgical instrument is attached by an adhesive to the surgical instrument, and wherein the hook and latch portion that is configured and adapted to be attached to a structure within the sterile field for parking the surgical instrument includes an adhesive layer covered with a removable cover configured to be removed for attachment of the surgical instrument within the sterile field.

5. A surgical device as recited in claim 1, wherein the surgical instrument is an instrument selected from the group consisting of electrocautery pencils, cauterizing forceps, surgical drills, suction devices, mono-polar or bi-polar RF cutting/coagulating instruments, and ultrasonic cutting/coagulating instruments.

6. A surgical device as recited in claim 1, wherein the surgical instrument is a cordless instrument selected from the group consisting of suturing instruments, clip appliers, and staplers.

\* \* \* \* \*